US008634889B2

(12) United States Patent
Al-Ali et al.

(10) Patent No.: US 8,634,889 B2
(45) Date of Patent: *Jan. 21, 2014

(54) CONFIGURABLE PHYSIOLOGICAL MEASUREMENT SYSTEM

(75) Inventors: Ammar Al-Ali, Tustin, CA (US); Joe E. Kiani, Laguna Hills, CA (US); Walter M. Weber, Laguna Hills, CA (US)

(73) Assignee: Cercacor Laboratories, Inc., Irvine, CA (US)

( * ) Notice: Subject to any disclaimer, the term of this patent is extended or adjusted under 35 U.S.C. 154(b) by 790 days.

This patent is subject to a terminal disclaimer.

(21) Appl. No.: 12/782,581

(22) Filed: May 18, 2010

(65) Prior Publication Data
US 2010/0228108 A1 Sep. 9, 2010

Related U.S. Application Data

(63) Continuation of application No. 11/367,036, filed on Mar. 1, 2006, now Pat. No. 7,729,733.

(60) Provisional application No. 60/657,596, filed on Mar. 1, 2005, provisional application No. 60/657,281, filed on Mar. 1, 2005, provisional application No. 60/657,268, filed on Mar. 1, 2005, provisional application No. 60/657,759, filed on Mar. 1, 2005.

(51) Int. Cl.
*A61B 5/1455* (2006.01)

(52) U.S. Cl.
USPC .......................................... 600/310

(58) Field of Classification Search
USPC .................... 600/300, 310, 322, 323
See application file for complete search history.

(56) References Cited

U.S. PATENT DOCUMENTS

| | | |
|---|---|---|
| 3,910,701 A | 10/1975 | Henderson et al. |
| 3,998,550 A | 12/1976 | Konishi et al. |
| 4,014,321 A | 3/1977 | March |
| 4,051,522 A | 9/1977 | Healy et al. |
| 4,157,708 A | 6/1979 | Imura |
| 4,167,331 A | 9/1979 | Nielsen |

(Continued)

FOREIGN PATENT DOCUMENTS

| | | |
|---|---|---|
| EP | 0 231 379 | 8/1987 |
| EP | 41 92 23 | 3/1991 |
| EP | 0 569 670 | 2/1993 |
| EP | 0 529 412 | 3/1993 |
| EP | 0 675 540 | 10/1995 |

(Continued)

OTHER PUBLICATIONS

Burritt, Mary F.; Current Analytical Approaches to Measuring Blood Analytes; vol. 36; No. 8(B); 1990.

(Continued)

*Primary Examiner* — Eric Winakur
(74) *Attorney, Agent, or Firm* — Knobbe Martens Olson & Bear LLP (57) ABSTRACT

A physiological measurement system has a sensor, a processor, a communications link and information elements. The sensor is configured to transmit light having a plurality of wavelengths into a tissue site and to generate a sensor signal responsive to the transmitted light after tissue attenuation. The attenuated light can be used by the system to determine a plurality of physiological measurements. The processor is configured to operate on the sensor signal so as to derive at least one physiological parameter after which of the plurality of physiological measurements the system is configured to or capable of measuring.

18 Claims, 5 Drawing Sheets

(56) References Cited

U.S. PATENT DOCUMENTS

| | | |
|---|---|---|
| 4,266,554 A | 5/1981 | Hamaguri |
| 4,267,844 A | 5/1981 | Yamanishi |
| 4,446,871 A | 5/1984 | Imura |
| 4,531,527 A | 7/1985 | Reinhold, Jr. et al. |
| 4,586,513 A | 5/1986 | Hamaguri |
| 4,621,643 A | 11/1986 | New et al. |
| 4,653,498 A | 3/1987 | New, Jr. et al. |
| 4,655,225 A | 4/1987 | Dahne et al. |
| 4,685,464 A | 8/1987 | Goldberger et al. |
| 4,694,833 A | 9/1987 | Hamaguri |
| 4,695,955 A * | 9/1987 | Faisandier .................. 600/300 |
| 4,700,708 A | 10/1987 | New et al. |
| 4,714,341 A | 12/1987 | Hamaguri et al. |
| 4,770,179 A | 9/1988 | New et al. |
| 4,773,422 A | 9/1988 | Isaacson et al. |
| 4,781,195 A | 11/1988 | Martin |
| 4,800,885 A | 1/1989 | Johnson |
| 4,805,623 A | 2/1989 | Jobsis |
| 4,832,484 A | 5/1989 | Aoyagi et al. |
| 4,846,183 A | 7/1989 | Martin |
| 4,854,328 A | 8/1989 | Pollack |
| 4,863,265 A | 9/1989 | Flower et al. |
| 4,867,571 A | 9/1989 | Frick et al. |
| 4,869,254 A | 9/1989 | Stone et al. |
| 4,907,876 A | 3/1990 | Suzuki et al. |
| 4,911,167 A | 3/1990 | Corenman et al. |
| 4,934,372 A | 6/1990 | Corenman et al. |
| 4,938,218 A | 7/1990 | Goodman et al. |
| 4,942,877 A | 7/1990 | Sakai et al. |
| 4,955,379 A | 9/1990 | Hall |
| 4,960,126 A | 10/1990 | Conlon et al. |
| 4,960,128 A | 10/1990 | Gordon et al. |
| 4,964,010 A | 10/1990 | Miyasaka et al. |
| 4,964,408 A | 10/1990 | Hink et al. |
| 4,967,571 A | 11/1990 | Sporri |
| 4,975,581 A | 12/1990 | Robinson et al. |
| 4,986,665 A | 1/1991 | Yamanishi et al. |
| 4,997,769 A | 3/1991 | Lundsgaard |
| 5,025,791 A | 6/1991 | Niwa |
| RE33,643 E | 7/1991 | Isaacson et al. |
| 5,028,787 A | 7/1991 | Rosenthal et al. |
| 5,033,472 A | 7/1991 | Sato et al. |
| 5,041,187 A | 8/1991 | Hink et al. |
| 5,054,495 A | 10/1991 | Uemura et al. |
| 5,058,588 A | 10/1991 | Kaestle et al. |
| 5,069,213 A | 12/1991 | Polczynski |
| 5,077,476 A | 12/1991 | Rosenthal |
| 5,078,136 A | 1/1992 | Stone et al. |
| 5,137,023 A | 8/1992 | Mendelson et al. |
| 5,163,438 A | 11/1992 | Gordon et al. |
| 5,189,609 A | 2/1993 | Tivig et al. |
| 5,190,040 A | 3/1993 | Aoyagi |
| 5,209,230 A | 5/1993 | Swedlow et al. |
| 5,226,053 A | 7/1993 | Cho et al. |
| 5,246,002 A | 9/1993 | Prosser |
| 5,247,931 A | 9/1993 | Norwood |
| 5,259,381 A | 11/1993 | Chung |
| 5,267,562 A | 12/1993 | Ukawa et al. |
| 5,267,563 A | 12/1993 | Swedlow et al. |
| 5,278,627 A | 1/1994 | Aoyagi |
| 5,297,548 A | 3/1994 | Pologe |
| 5,313,940 A | 5/1994 | Fuse et al. |
| 5,319,355 A | 6/1994 | Russek |
| 5,331,549 A | 7/1994 | Crawford, Jr. |
| 5,335,659 A | 8/1994 | Pologe et al. |
| 5,337,744 A | 8/1994 | Branigan |
| 5,337,745 A | 8/1994 | Benaron |
| 5,341,805 A | 8/1994 | Stavridi et al. |
| 5,348,004 A | 9/1994 | Hollub |
| 5,351,685 A | 10/1994 | Potratz |
| 5,355,880 A | 10/1994 | Thomas et al. |
| 5,355,882 A | 10/1994 | Ukawa et al. |
| 5,361,758 A | 11/1994 | Hall et al. |
| 5,368,224 A | 11/1994 | Richardson et al. |
| D353,195 S | 12/1994 | Savage et al. |
| D353,196 S | 12/1994 | Savage et al. |
| 5,372,136 A | 12/1994 | Steuer et al. |
| 5,377,676 A | 1/1995 | Vari et al. |
| 5,385,143 A | 1/1995 | Aoyagi |
| 5,387,122 A | 2/1995 | Goldberger et al. |
| 5,392,777 A | 2/1995 | Swedlow et al. |
| 5,413,101 A | 5/1995 | Sugiura |
| D359,546 S | 6/1995 | Savage et al. |
| 5,421,329 A | 6/1995 | Casciani et al. |
| 5,424,545 A | 6/1995 | Block et al. |
| 5,427,093 A | 6/1995 | Ogawa et al. |
| 5,429,128 A | 7/1995 | Cadell et al. |
| 5,431,170 A | 7/1995 | Mathews |
| 5,435,309 A | 7/1995 | Thomas et al. |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| RE35,122 E | 12/1995 | Corenman et al. |
| 5,482,036 A | 1/1996 | Diab et al. |
| 5,490,505 A | 2/1996 | Diab et al. |
| 5,490,523 A | 2/1996 | Isaacson et al. |
| 5,494,032 A | 2/1996 | Robinson et al. |
| 5,494,043 A | 2/1996 | O'Sullivan et al. |
| 5,503,148 A | 4/1996 | Pologe et al. |
| 5,520,177 A | 5/1996 | Ogawa |
| 5,533,507 A | 7/1996 | Potratz |
| 5,533,511 A | 7/1996 | Kaspari et al. |
| 5,534,851 A | 7/1996 | Russek |
| 5,551,423 A | 9/1996 | Sugiura |
| 5,553,615 A | 9/1996 | Carim et al. |
| 5,555,882 A | 9/1996 | Richardson et al. |
| 5,561,275 A | 10/1996 | Savage et al. |
| 5,562,002 A | 10/1996 | Lalin |
| 5,575,284 A | 11/1996 | Athan et al. |
| 5,577,500 A | 11/1996 | Potratz |
| 5,584,299 A | 12/1996 | Sakai et al. |
| 5,588,427 A | 12/1996 | Tien |
| 5,590,649 A | 1/1997 | Caro et al. |
| 5,590,652 A | 1/1997 | Inai |
| 5,595,176 A | 1/1997 | Yamaura |
| 5,596,992 A | 1/1997 | Haaland et al. |
| 5,602,924 A | 2/1997 | Durand et al. |
| 5,603,623 A | 2/1997 | Nishikawa et al. |
| 5,630,413 A | 5/1997 | Thomas et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,059 A | 7/1997 | Fein et al. |
| 5,645,060 A | 7/1997 | Yorkey |
| 5,645,440 A | 7/1997 | Tobler et al. |
| 5,660,567 A | 8/1997 | Nierlich et al. |
| 5,662,106 A | 9/1997 | Swedlow et al. |
| 5,676,139 A | 10/1997 | Goldberger et al. |
| 5,676,141 A | 10/1997 | Hollub |
| 5,678,544 A | 10/1997 | Delonzor et al. |
| 5,685,299 A | 11/1997 | Diab et al. |
| 5,685,301 A | 11/1997 | Klomhaus |
| 5,687,719 A | 11/1997 | Sato et al. |
| 5,687,722 A | 11/1997 | Tien et al. |
| 5,690,104 A | 11/1997 | Kanemoto et al. |
| 5,692,503 A | 12/1997 | Kuenstner |
| 5,697,371 A | 12/1997 | Aoyagi |
| 5,713,355 A | 2/1998 | Richardson et al. |
| 5,719,589 A | 2/1998 | Norman et al. |
| 5,720,284 A | 2/1998 | Aoyagi et al. |
| D393,830 S | 4/1998 | Tobler et al. |
| 5,743,262 A | 4/1998 | Lepper, Jr. et al. |
| 5,743,263 A | 4/1998 | Baker, Jr. |
| 5,746,206 A | 5/1998 | Mannheimer |
| 5,746,697 A | 5/1998 | Swedlow et al. |
| 5,752,914 A | 5/1998 | Delonzor et al. |
| 5,755,226 A | 5/1998 | Carim et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,772,587 A | 6/1998 | Gratton et al. |
| 5,779,630 A | 7/1998 | Fein et al. |

(56) References Cited

U.S. PATENT DOCUMENTS

| | | |
|---|---|---|
| 5,782,237 A | 7/1998 | Casciani et al. |
| 5,782,756 A | 7/1998 | Mannheimer |
| 5,782,757 A | 7/1998 | Diab et al. |
| 5,785,659 A | 7/1998 | Caro et al. |
| 5,790,729 A | 8/1998 | Pologe et al. |
| 5,791,347 A | 8/1998 | Flaherty et al. |
| 5,792,052 A | 8/1998 | Isaacson et al. |
| 5,793,485 A | 8/1998 | Gourley |
| 5,800,348 A | 9/1998 | Kaestle et al. |
| 5,800,349 A | 9/1998 | Isaacson et al. |
| 5,803,910 A | 9/1998 | Potratz |
| 5,807,246 A | 9/1998 | Sakaguchi et al. |
| 5,807,247 A | 9/1998 | Merchant et al. |
| 5,810,723 A | 9/1998 | Aldrich |
| 5,810,724 A | 9/1998 | Gronvall |
| 5,810,734 A | 9/1998 | Caro et al. |
| 5,817,010 A | 10/1998 | Hibl |
| 5,818,985 A | 10/1998 | Merchant et al. |
| 5,823,950 A | 10/1998 | Diab et al. |
| 5,823,952 A | 10/1998 | Levinson et al. |
| 5,827,182 A | 10/1998 | Raley et al. |
| 5,830,131 A | 11/1998 | Caro et al. |
| 5,830,137 A | 11/1998 | Sharf |
| 5,833,618 A | 11/1998 | Caro et al. |
| 5,839,439 A | 11/1998 | Nierlich et al. |
| RE36,000 E | 12/1998 | Swedlow et al. |
| 5,842,979 A | 12/1998 | Jarman |
| 5,851,178 A | 12/1998 | Aronow |
| 5,851,179 A | 12/1998 | Ritson et al. |
| 5,853,364 A | 12/1998 | Baker, Jr. et al. |
| 5,857,462 A | 1/1999 | Thomas et al. |
| 5,860,919 A | 1/1999 | Kiani-Azarbayjany et al. |
| 5,865,736 A | 2/1999 | Baker, Jr. et al. |
| 5,876,348 A | 3/1999 | Sugo |
| 5,885,213 A | 3/1999 | Richardson et al. |
| 5,890,929 A | 4/1999 | Mills et al. |
| 5,891,022 A | 4/1999 | Pologe |
| 5,891,024 A | 4/1999 | Jarman et al. |
| 5,904,654 A | 5/1999 | Wohltmann et al. |
| 5,910,108 A | 6/1999 | Solenberger |
| 5,916,154 A | 6/1999 | Hobbs et al. |
| 5,919,133 A | 7/1999 | Taylor |
| 5,919,134 A | 7/1999 | Diab |
| 5,921,921 A | 7/1999 | Potratz et al. |
| 5,934,277 A | 8/1999 | Mortz |
| 5,934,925 A | 8/1999 | Tobler et al. |
| 5,940,182 A | 8/1999 | Lepper, Jr. et al. |
| 5,954,644 A | 9/1999 | Dettling |
| 5,978,691 A | 11/1999 | Mills |
| 5,983,122 A | 11/1999 | Jarman et al. |
| 5,995,855 A | 11/1999 | Kiani et al. |
| 5,995,856 A | 11/1999 | Mannheimer et al. |
| 5,995,859 A | 11/1999 | Takahashi |
| 5,997,343 A | 12/1999 | Mills et al. |
| 5,999,841 A | 12/1999 | Aoyagi et al. |
| 6,002,952 A | 12/1999 | Diab et al. |
| 6,006,119 A | 12/1999 | Soller et al. |
| 6,011,986 A | 1/2000 | Diab et al. |
| 6,014,576 A | 1/2000 | Raley |
| 6,018,673 A | 1/2000 | Chin et al. |
| 6,018,674 A | 1/2000 | Aronow |
| 6,023,541 A | 2/2000 | Merchant et al. |
| 6,027,452 A | 2/2000 | Flaherty et al. |
| 6,036,642 A | 3/2000 | Diab et al. |
| 6,045,509 A | 4/2000 | Caro et al. |
| 6,064,898 A | 5/2000 | Aldrich |
| 6,067,462 A | 5/2000 | Diab et al. |
| 6,068,594 A | 5/2000 | Schloemer et al. |
| 6,073,037 A | 6/2000 | Alam et al. |
| 6,081,735 A | 6/2000 | Diab et al. |
| 6,083,172 A | 7/2000 | Baker, Jr. et al. |
| 6,088,607 A | 7/2000 | Diab et al. |
| 6,094,592 A | 7/2000 | Yorkey et al. |
| 6,104,938 A | 8/2000 | Huiku |
| 6,110,522 A | 8/2000 | Lepper, Jr. et al. |
| 6,112,107 A | 8/2000 | Hannula |
| 6,122,042 A | 9/2000 | Wunderman et al. |
| 6,124,597 A | 9/2000 | Shehada et al. |
| 6,129,675 A | 10/2000 | Jay |
| 6,144,868 A | 11/2000 | Parker |
| 6,149,588 A | 11/2000 | Noda et al. |
| 6,151,516 A | 11/2000 | Kiani-Azarbayjany et al. |
| 6,151,518 A | 11/2000 | Hayashi |
| 6,152,754 A | 11/2000 | Gerhardt et al. |
| 6,154,667 A | 11/2000 | Miura et al. |
| 6,157,041 A | 12/2000 | Thomas et al. |
| 6,157,850 A | 12/2000 | Diab et al. |
| 6,165,005 A | 12/2000 | Mills et al. |
| 6,174,283 B1 | 1/2001 | Nevo et al. |
| 6,184,521 B1 | 2/2001 | Coffin et al. |
| 6,192,261 B1 | 2/2001 | Gratton et al. |
| 6,206,830 B1 | 3/2001 | Diab et al. |
| 6,226,539 B1 | 5/2001 | Potratz |
| 6,229,856 B1 | 5/2001 | Diab et al. |
| 6,230,035 B1 | 5/2001 | Aoyagi et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,248,083 B1 | 6/2001 | Smith et al. |
| 6,253,097 B1 | 6/2001 | Aronow et al. |
| 6,256,523 B1 | 7/2001 | Diab et al. |
| 6,262,698 B1 | 7/2001 | Blum |
| 6,263,222 B1 | 7/2001 | Diab et al. |
| 6,272,363 B1 | 8/2001 | Casciani et al. |
| 6,278,522 B1 | 8/2001 | Lepper, Jr. et al. |
| 6,280,213 B1 | 8/2001 | Tobler et al. |
| 6,285,895 B1 | 9/2001 | Ristolainen et al. |
| 6,285,896 B1 | 9/2001 | Tobler et al. |
| 6,298,252 B1 | 10/2001 | Kovach et al. |
| 6,304,675 B1 | 10/2001 | Osbourn et al. |
| 6,304,767 B1 | 10/2001 | Soller et al. |
| 6,321,100 B1 | 11/2001 | Parker |
| 6,325,761 B1 | 12/2001 | Jay |
| 6,330,468 B1 | 12/2001 | Scharf |
| 6,334,065 B1 | 12/2001 | Al-Ali et al. |
| 6,341,257 B1 | 1/2002 | Haaland |
| 6,343,224 B1 | 1/2002 | Parker |
| 6,349,228 B1 | 2/2002 | Kiani et al. |
| 6,351,658 B1 | 2/2002 | Middleman et al. |
| 6,356,774 B1 | 3/2002 | Bernstein et al. |
| 6,360,113 B1 | 3/2002 | Dettling |
| 6,360,114 B1 | 3/2002 | Diab et al. |
| 6,363,269 B1 | 3/2002 | Hanna et al. |
| 6,368,283 B1 | 4/2002 | Xu et al. |
| 6,371,921 B1 | 4/2002 | Caro et al. |
| 6,374,129 B1 | 4/2002 | Chin et al. |
| 6,377,828 B1 | 4/2002 | Chaiken et al. |
| 6,377,829 B1 | 4/2002 | Al-Ali |
| 6,388,240 B2 | 5/2002 | Schulz et al. |
| 6,393,310 B1 | 5/2002 | Kuenstner |
| 6,397,091 B2 | 5/2002 | Diab et al. |
| 6,397,092 B1 | 5/2002 | Norris et al. |
| 6,397,093 B1 | 5/2002 | Aldrich |
| 6,408,198 B1 | 6/2002 | Hanna et al. |
| 6,411,833 B1 | 6/2002 | Baker, Jr. et al. |
| 6,415,166 B1 | 7/2002 | Van Hoy et al. |
| 6,415,233 B1 | 7/2002 | Haaland |
| 6,415,236 B2 | 7/2002 | Kobayashi et al. |
| 6,421,549 B1 | 7/2002 | Jacques |
| 6,430,525 B1 | 8/2002 | Weber et al. |
| 6,434,408 B1 | 8/2002 | Heckel |
| 6,441,388 B1 | 8/2002 | Thomas et al. |
| 6,453,184 B1 | 9/2002 | Hyogo et al. |
| 6,455,340 B1 | 9/2002 | Chua et al. |
| 6,463,310 B1 | 10/2002 | Swedlow et al. |
| 6,463,311 B1 | 10/2002 | Diab |
| 6,466,824 B1 | 10/2002 | Struble |
| 6,470,199 B1 | 10/2002 | Kopotic et al. |
| 6,480,729 B2 | 11/2002 | Stone |
| 6,490,466 B1 | 12/2002 | Fein et al. |
| 6,497,659 B1 | 12/2002 | Rafert |
| 6,501,974 B2 | 12/2002 | Huiku |
| 6,501,975 B2 | 12/2002 | Diab et al. |
| 6,504,943 B1 | 1/2003 | Sweatt et al. |

(56) References Cited

U.S. PATENT DOCUMENTS

| | | |
|---|---|---|
| 6,505,059 B1 | 1/2003 | Kollias et al. |
| 6,505,060 B1 | 1/2003 | Norris |
| 6,505,061 B2 | 1/2003 | Larson |
| 6,505,133 B1 | 1/2003 | Hanna |
| 6,510,329 B2 | 1/2003 | Heckel |
| 6,515,273 B2 | 2/2003 | Al-Ali |
| 6,519,486 B1 | 2/2003 | Edgar, Jr. et al. |
| 6,519,487 B1 | 2/2003 | Parker |
| 6,522,398 B2 | 2/2003 | Cadell et al. |
| 6,525,386 B1 | 2/2003 | Mills et al. |
| 6,526,300 B1 | 2/2003 | Kiani et al. |
| 6,526,301 B2 | 2/2003 | Larsen et al. |
| 6,528,809 B1 | 3/2003 | Thomas et al. |
| 6,537,225 B1 | 3/2003 | Mills |
| 6,541,756 B2 | 4/2003 | Schulz et al. |
| 6,542,763 B1 | 4/2003 | Yamashita et al. |
| 6,542,764 B1 | 4/2003 | Al-Ali et al. |
| 6,545,652 B1 | 4/2003 | Tsuji |
| 6,546,267 B1 | 4/2003 | Sugiura |
| 6,553,241 B2 | 4/2003 | Mannheimer et al. |
| 6,564,077 B2 | 5/2003 | Mortara |
| 6,571,113 B1 | 5/2003 | Fein et al. |
| 6,580,086 B1 | 6/2003 | Schulz et al. |
| 6,582,964 B1 | 6/2003 | Samsoondar et al. |
| 6,584,336 B1 | 6/2003 | Ali et al. |
| 6,584,413 B1 | 6/2003 | Keenan et al. |
| 6,591,123 B2 | 7/2003 | Fein et al. |
| 6,594,511 B2 | 7/2003 | Stone et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,600,940 B1 | 7/2003 | Fein et al. |
| 6,606,509 B2 | 8/2003 | Schmitt |
| 6,606,510 B2 | 8/2003 | Swedlow et al. |
| 6,606,511 B1 | 8/2003 | Ali et al. |
| 6,609,016 B1 | 8/2003 | Lynn |
| 6,611,698 B1 | 8/2003 | Yamashita et al. |
| 6,614,521 B2 | 9/2003 | Samsoondar et al. |
| 6,615,064 B1 | 9/2003 | Aldrich |
| 6,615,151 B1 | 9/2003 | Scecina et al. |
| 6,618,602 B1 | 9/2003 | Levin |
| 6,622,095 B2 | 9/2003 | Kobayashi et al. |
| 6,628,975 B1 | 9/2003 | Fein et al. |
| 6,631,281 B1 | 10/2003 | Kastle |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,623 B1 | 11/2003 | Kastle |
| 6,654,624 B2 | 11/2003 | Diab et al. |
| 6,657,717 B2 | 12/2003 | Cadell et al. |
| 6,658,276 B2 | 12/2003 | Kianl et al. |
| 6,658,277 B2 | 12/2003 | Wasserman |
| 6,661,161 B1 | 12/2003 | Lanzo et al. |
| 6,662,033 B2 | 12/2003 | Casciani et al. |
| 6,665,551 B1 | 12/2003 | Suzuki |
| 6,668,183 B2 | 12/2003 | Hicks et al. |
| 6,671,526 B1 | 12/2003 | Aoyagi et al. |
| 6,671,531 B2 | 12/2003 | Al-Ali et al. |
| 6,675,031 B1 | 1/2004 | Porges et al. |
| 6,675,106 B1 | 1/2004 | Keenan et al. |
| 6,678,543 B2 | 1/2004 | Diab et al. |
| 6,681,126 B2 | 1/2004 | Solenberger |
| 6,684,090 B2 | 1/2004 | Ali et al. |
| 6,684,091 B2 | 1/2004 | Parker |
| 6,687,620 B1 | 2/2004 | Haaland et al. |
| 6,690,466 B2 | 2/2004 | Miller et al. |
| 6,694,157 B1 | 2/2004 | Stone et al. |
| 6,697,655 B2 | 2/2004 | Sueppel et al. |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,701,170 B2 | 3/2004 | Stetson |
| 6,708,049 B1 | 3/2004 | Berson et al. |
| 6,711,503 B2 | 3/2004 | Haaland |
| 6,714,803 B1 | 3/2004 | Mortz |
| 6,714,804 B2 | 3/2004 | Al-Ali et al. |
| 6,714,805 B2 | 3/2004 | Jeon et al. |
| RE38,492 E | 4/2004 | Diab et al. |
| 6,719,705 B2 | 4/2004 | Mills |
| 6,720,734 B2 | 4/2004 | Norris |
| 6,721,582 B2 | 4/2004 | Trepagnier et al. |
| 6,721,584 B2 | 4/2004 | Baker, Jr. et al. |
| 6,721,585 B1 | 4/2004 | Parker |
| 6,725,074 B1 | 4/2004 | Kastle |
| 6,725,075 B2 | 4/2004 | Al-Ali |
| 6,726,634 B2 | 4/2004 | Freeman |
| 6,728,560 B2 | 4/2004 | Kollias et al. |
| 6,735,459 B2 | 5/2004 | Parker |
| 6,741,875 B1 | 5/2004 | Pawluczyk et al. |
| 6,741,876 B1 | 5/2004 | Scecina et al. |
| 6,743,172 B1 | 6/2004 | Blike |
| 6,745,060 B2 | 6/2004 | Diab et al. |
| 6,745,061 B1 | 6/2004 | Hicks et al. |
| 6,748,253 B2 | 6/2004 | Norris et al. |
| 6,748,254 B2 | 6/2004 | O'Neil et al. |
| 6,754,515 B1 | 6/2004 | Pologe |
| 6,754,516 B2 | 6/2004 | Mannheimer |
| 6,760,607 B2 | 7/2004 | Al-Ali |
| 6,760,609 B2 | 7/2004 | Jacques |
| 6,770,028 B1 | 8/2004 | Ali et al. |
| 6,771,994 B2 | 8/2004 | Kiani et al. |
| 6,773,397 B2 | 8/2004 | Kelly |
| 6,778,923 B2 | 8/2004 | Norris et al. |
| 6,780,158 B2 | 8/2004 | Yarita |
| 6,788,849 B1 | 9/2004 | Pawluczyk |
| 6,792,300 B1 | 9/2004 | Diab et al. |
| 6,800,373 B2 | 10/2004 | Gorczyca |
| 6,801,797 B2 | 10/2004 | Mannheimer et al. |
| 6,801,799 B2 | 10/2004 | Mendelson |
| 6,810,277 B2 | 10/2004 | Edgar, Jr. et al. |
| 6,813,511 B2 | 11/2004 | Diab et al. |
| 6,816,741 B2 | 11/2004 | Diab |
| 6,819,950 B2 | 11/2004 | Mills |
| 6,822,564 B2 | 11/2004 | Al-Ali |
| 6,825,619 B2 | 11/2004 | Norris |
| 6,826,419 B2 | 11/2004 | Diab et al. |
| 6,829,496 B2 | 12/2004 | Nagai et al. |
| 6,829,501 B2 | 12/2004 | Nielsen et al. |
| 6,830,711 B2 | 12/2004 | Mills et al. |
| 6,836,679 B2 | 12/2004 | Baker, Jr. et al. |
| 6,839,579 B1 | 1/2005 | Chin |
| 6,839,580 B2 | 1/2005 | Zonios et al. |
| 6,839,582 B2 | 1/2005 | Heckel |
| 6,842,702 B2 | 1/2005 | Haaland et al. |
| 6,845,256 B2 | 1/2005 | Chin et al. |
| 6,847,835 B1 | 1/2005 | Yamanishi |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,861,641 B1 | 3/2005 | Adams |
| 6,869,402 B2 | 3/2005 | Arnold |
| 6,882,874 B2 | 4/2005 | Huiku |
| 6,898,452 B2 | 5/2005 | Al-Ali et al. |
| 6,912,049 B2 | 6/2005 | Pawluczyk et al. |
| 6,917,422 B2 | 7/2005 | Samsoondar et al. |
| 6,919,566 B1 | 7/2005 | Cadell |
| 6,920,345 B2 | 7/2005 | Al-Ali et al. |
| 6,921,367 B2 | 7/2005 | Mills |
| 6,922,645 B2 | 7/2005 | Haaland et al. |
| 6,928,311 B1 | 8/2005 | Pawluczyk et al. |
| 6,931,268 B1 | 8/2005 | Kiani-Azarbayjany et al. |
| 6,931,269 B2 | 8/2005 | Terry |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,944,487 B2 | 9/2005 | Maynard et al. |
| 6,950,687 B2 | 9/2005 | Al-Ali |
| 6,956,572 B2 | 10/2005 | Zaleski |
| 6,961,598 B2 | 11/2005 | Diab |

(56) References Cited

U.S. PATENT DOCUMENTS

| | | | |
|---|---|---|---|
| 6,970,792 B1 | 11/2005 | Diab | |
| 6,975,891 B2 | 12/2005 | Pawluczyk | |
| 6,979,812 B2 | 12/2005 | Al-Ali | |
| 6,985,764 B2 | 1/2006 | Mason et al. | |
| 6,987,994 B1 | 1/2006 | Mortz | |
| 6,993,371 B2 | 1/2006 | Kiani et al. | |
| 6,996,427 B2 | 2/2006 | Ali et al. | |
| 6,999,904 B2 | 2/2006 | Weber et al. | |
| 7,001,337 B2 | 2/2006 | Dekker | |
| 7,003,338 B2 | 2/2006 | Weber et al. | |
| 7,003,339 B2 | 2/2006 | Diab et al. | |
| 7,006,856 B2 | 2/2006 | Baker, Jr. et al. | |
| 7,015,451 B2 | 3/2006 | Dalke et al. | |
| 7,024,233 B2 | 4/2006 | Ali et al. | |
| 7,027,849 B2 | 4/2006 | Al-Ali | |
| 7,030,749 B2 | 4/2006 | Al-Ali | |
| 7,039,449 B2 | 5/2006 | Al-Ali | |
| 7,041,060 B2 | 5/2006 | Flaherty et al. | |
| 7,044,918 B2 | 5/2006 | Diab | |
| 7,067,893 B2 | 6/2006 | Mills et al. | |
| 7,096,052 B2 | 8/2006 | Mason et al. | |
| 7,096,054 B2 | 8/2006 | Abdul-Hafiz et al. | |
| 7,132,641 B2 | 11/2006 | Schulz et al. | |
| 7,142,901 B2 | 11/2006 | Kiani et al. | |
| 7,149,561 B2 | 12/2006 | Diab | |
| 7,186,966 B2 | 3/2007 | Al-Ali | |
| 7,190,261 B2 | 3/2007 | Al-Ali | |
| 7,215,984 B2 | 5/2007 | Diab et al. | |
| 7,215,986 B2 | 5/2007 | Diab et al. | |
| 7,221,971 B2 | 5/2007 | Diab et al. | |
| 7,225,006 B2 | 5/2007 | Al-Ali et al. | |
| 7,225,007 B2 | 5/2007 | Al-Ali et al. | |
| RE39,672 E | 6/2007 | Shehada et al. | |
| 7,239,905 B2 | 7/2007 | Kiani-Azarbayjany et al. | |
| 7,245,953 B1 | 7/2007 | Parker | |
| 7,254,429 B2 | 8/2007 | Schurman et al. | |
| 7,254,431 B2 | 8/2007 | Al-Ali et al. | |
| 7,254,433 B2 | 8/2007 | Diab et al. | |
| 7,254,434 B2 | 8/2007 | Schulz et al. | |
| 7,272,425 B2 | 9/2007 | Al-Ali | |
| 7,274,955 B2 | 9/2007 | Kiani et al. | |
| D554,263 S | 10/2007 | Al-Ali | |
| 7,280,858 B2 | 10/2007 | Al-Ali et al. | |
| 7,289,835 B2 | 10/2007 | Mansfield et al. | |
| 7,292,883 B2 | 11/2007 | De Felice et al. | |
| 7,295,866 B2 | 11/2007 | Al-Ali | |
| 7,299,080 B2 | 11/2007 | Acosta et al. | |
| 7,328,053 B1 | 2/2008 | Diab et al. | |
| 7,332,784 B2 | 2/2008 | Mills et al. | |
| 7,340,287 B2 | 3/2008 | Mason et al. | |
| 7,341,559 B2 | 3/2008 | Schulz et al. | |
| 7,343,186 B2 | 3/2008 | Lamego et al. | |
| D566,282 S | 4/2008 | Al-Ali et al. | |
| 7,355,512 B1 | 4/2008 | Al-Ali | |
| 7,356,365 B2 | 4/2008 | Schurman | |
| 7,371,981 B2 | 5/2008 | Abdul-Hafiz | |
| 7,373,193 B2 | 5/2008 | Al-Ali et al. | |
| 7,373,194 B2 | 5/2008 | Weber et al. | |
| 7,376,453 B1 | 5/2008 | Diab et al. | |
| 7,377,794 B2 | 5/2008 | Al-Ali et al. | |
| 7,377,899 B2 | 5/2008 | Weber et al. | |
| 7,383,070 B2 | 6/2008 | Diab et al. | |
| 7,415,297 B2 | 8/2008 | Al-Ali et al. | |
| 7,428,432 B2 | 9/2008 | Ali et al. | |
| 7,438,683 B2 | 10/2008 | Al-Ali et al. | |
| 7,440,787 B2 | 10/2008 | Diab | |
| 7,454,240 B2 | 11/2008 | Diab et al. | |
| 7,467,002 B2 | 12/2008 | Weber et al. | |
| 7,469,157 B2 | 12/2008 | Diab et al. | |
| 7,471,969 B2 | 12/2008 | Diab et al. | |
| 7,471,971 B2 | 12/2008 | Diab et al. | |
| 7,483,729 B2 | 1/2009 | Al-Ali et al. | |
| 7,483,730 B2 | 1/2009 | Diab et al. | |
| 7,489,958 B2 | 2/2009 | Diab et al. | |
| 7,496,391 B2 | 2/2009 | Diab et al. | |
| 7,496,393 B2 | 2/2009 | Diab et al. | |
| D587,657 S | 3/2009 | Al-Ali et al. | |
| 7,499,741 B2 | 3/2009 | Diab et al. | |
| 7,499,835 B2 | 3/2009 | Weber et al. | |
| 7,500,950 B2 | 3/2009 | Al-Ali et al. | |
| 7,509,154 B2 | 3/2009 | Diab et al. | |
| 7,509,494 B2 | 3/2009 | Al-Ali | |
| 7,510,849 B2 | 3/2009 | Schurman et al. | |
| 7,526,328 B2 | 4/2009 | Diab et al. | |
| 7,530,942 B1 | 5/2009 | Diab | |
| 7,530,949 B2 | 5/2009 | Al Ali et al. | |
| 7,530,955 B2 | 5/2009 | Diab et al. | |
| 7,563,110 B2 | 7/2009 | Al-Ali et al. | |
| 7,596,398 B2 | 9/2009 | Al-Ali et al. | |
| 7,618,375 B2 | 11/2009 | Flaherty et al. | |
| D606,659 S | 12/2009 | Kiani et al. | |
| 7,647,083 B2 | 1/2010 | Al-Ali et al. | |
| D609,193 S | 2/2010 | Al-Ali et al. | |
| 7,670,726 B2 | 3/2010 | Lu | |
| D614,305 S | 4/2010 | Al-Ali et al. | |
| RE41,317 E | 5/2010 | Parker | |
| 7,729,733 B2 | 6/2010 | Al-Ali et al. | |
| 7,734,320 B2 | 6/2010 | Al-Ali | |
| 7,761,127 B2 | 7/2010 | Al-Ali et al. | |
| 7,761,128 B2 | 7/2010 | Al-Ali et al. | |
| 7,764,982 B2 | 7/2010 | Dalke et al. | |
| D621,516 S | 8/2010 | Kiani et al. | |
| 7,791,155 B2 | 9/2010 | Diab | |
| 7,801,581 B2 | 9/2010 | Diab | |
| 7,822,452 B2 | 10/2010 | Schurman et al. | |
| RE41,912 E | 11/2010 | Parker | |
| 7,844,313 B2 | 11/2010 | Kiani et al. | |
| 7,844,314 B2 | 11/2010 | Al-Ali | |
| 7,844,315 B2 | 11/2010 | Al-Ali | |
| 7,865,222 B2 | 1/2011 | Weber et al. | |
| 7,899,507 B2 | 3/2011 | Al-Ali et al. | |
| 7,957,780 B2 | 6/2011 | Lamego et al. | |
| 8,130,105 B2 | 3/2012 | Al-Ali et al. | |
| 8,190,223 B2 | 5/2012 | Al-Ali et al. | |
| 8,224,411 B2 | 7/2012 | Al-Ali et al. | |
| 8,255,027 B2 | 8/2012 | Al-Ali et al. | |
| 8,385,996 B2 | 2/2013 | Dalke et al. | |
| 2001/0044700 A1 | 11/2001 | Kobayashi et al. | |
| 2001/0045532 A1 | 11/2001 | Schulz et al. | |
| 2002/0021269 A1 | 2/2002 | Rast | |
| 2002/0026107 A1 | 2/2002 | Kiani et al. | |
| 2002/0035318 A1 | 3/2002 | Mannheimer et al. | |
| 2002/0038078 A1 | 3/2002 | Ito | |
| 2002/0038081 A1 | 3/2002 | Fein et al. | |
| 2002/0051290 A1 | 5/2002 | Hannington | |
| 2002/0059047 A1 | 5/2002 | Haaland | |
| 2002/0082488 A1 | 6/2002 | Al-Ali et al. | |
| 2002/0095078 A1 | 7/2002 | Mannheimer et al. | |
| 2002/0111748 A1 | 8/2002 | Kobayashi et al. | |
| 2002/0115919 A1 | 8/2002 | Al-Ali | |
| 2002/0154665 A1 | 10/2002 | Funabashi et al. | |
| 2002/0156353 A1 | 10/2002 | Larson | |
| 2002/0159002 A1 | 10/2002 | Chang | |
| 2002/0161291 A1 | 10/2002 | Kiani et al. | |
| 2002/0165440 A1 | 11/2002 | Mason et al. | |
| 2002/0183819 A1 | 12/2002 | Struble | |
| 2003/0045784 A1 | 3/2003 | Palatnik et al. | |
| 2003/0045785 A1 | 3/2003 | Diab et al. | |
| 2003/0049232 A1 | 3/2003 | Page et al. | |
| 2003/0109775 A1 | 6/2003 | O'Neil et al. | |
| 2003/0116769 A1 | 6/2003 | Song et al. | |
| 2003/0117296 A1 | 6/2003 | Seely | |
| 2003/0120160 A1 | 6/2003 | Yarita | |
| 2003/0120164 A1 | 6/2003 | Nielsen et al. | |
| 2003/0135099 A1 | 7/2003 | Al-Ali | |
| 2003/0139657 A1 | 7/2003 | Solenberger | |
| 2003/0160257 A1 | 8/2003 | Bader et al. | |
| 2003/0195402 A1 | 10/2003 | Fein et al. | |
| 2004/0006261 A1 | 1/2004 | Swedlow et al. | |
| 2004/0033618 A1 | 2/2004 | Haass et al. | |
| 2004/0059209 A1 | 3/2004 | Al Ali et al. | |
| 2004/0064259 A1 | 4/2004 | Haaland et al. | |
| 2004/0081621 A1 | 4/2004 | Arndt et al. | |
| 2004/0092805 A1 | 5/2004 | Yarita | |

(56) References Cited

U.S. PATENT DOCUMENTS

| | | |
|---|---|---|
| 2004/0133087 A1 | 7/2004 | Ali et al. |
| 2004/0138538 A1 | 7/2004 | Stetson |
| 2004/0138540 A1 | 7/2004 | Baker, Jr. et al. |
| 2004/0147822 A1 | 7/2004 | Al-Ali et al. |
| 2004/0147823 A1 | 7/2004 | Kiani et al. |
| 2004/0158132 A1 | 8/2004 | Zaleski |
| 2004/0158134 A1 | 8/2004 | Diab et al. |
| 2004/0158135 A1 | 8/2004 | Baker, Jr. et al. |
| 2004/0158162 A1 | 8/2004 | Narimatsu |
| 2004/0162472 A1 | 8/2004 | Berson et al. |
| 2004/0167382 A1 | 8/2004 | Gardner et al. |
| 2004/0171940 A1 | 9/2004 | Narimatsu |
| 2004/0176670 A1 | 9/2004 | Takamura et al. |
| 2004/0181134 A1 | 9/2004 | Baker, Jr. et al. |
| 2004/0199063 A1 | 10/2004 | O'Neil et al. |
| 2004/0204639 A1 | 10/2004 | Casciani et al. |
| 2004/0204868 A1 | 10/2004 | Maynard et al. |
| 2004/0229391 A1 | 11/2004 | Ohya et al. |
| 2004/0262046 A1 | 12/2004 | Simon et al. |
| 2004/0267103 A1 | 12/2004 | Li et al. |
| 2004/0267140 A1 | 12/2004 | Ito et al. |
| 2005/0033128 A1 | 2/2005 | Al Ali et al. |
| 2005/0043902 A1 | 2/2005 | Haaland et al. |
| 2005/0049469 A1 | 3/2005 | Aoyagi et al. |
| 2005/0054908 A1 | 3/2005 | Blank et al. |
| 2005/0070773 A1 | 3/2005 | Chin et al. |
| 2005/0070775 A1 | 3/2005 | Chin et al. |
| 2005/0075546 A1 | 4/2005 | Samsoondar et al. |
| 2005/0085704 A1 | 4/2005 | Schulz et al. |
| 2005/0085735 A1 | 4/2005 | Baker, Jr. et al. |
| 2005/0124871 A1 | 6/2005 | Baker, Jr. et al. |
| 2005/0143634 A1 | 6/2005 | Baker, Jr. et al. |
| 2005/0143943 A1 | 6/2005 | Brown |
| 2005/0148834 A1 | 7/2005 | Hull et al. |
| 2005/0184895 A1 | 8/2005 | Petersen et al. |
| 2005/0187447 A1 | 8/2005 | Chew et al. |
| 2005/0187448 A1 | 8/2005 | Petersen et al. |
| 2005/0187449 A1 | 8/2005 | Chew et al. |
| 2005/0187450 A1 | 8/2005 | Chew et al. |
| 2005/0187452 A1 | 8/2005 | Petersen et al. |
| 2005/0187453 A1 | 8/2005 | Petersen et al. |
| 2005/0197549 A1 | 9/2005 | Baker, Jr. |
| 2005/0197579 A1 | 9/2005 | Baker, Jr. |
| 2005/0197793 A1 | 9/2005 | Baker, Jr. |
| 2005/0203357 A1 | 9/2005 | Debreczeny et al. |
| 2005/0209515 A1 | 9/2005 | Hockersmith et al. |
| 2005/0228253 A1 | 10/2005 | Debreczeny |
| 2005/0250997 A1 | 11/2005 | Takedo et al. |
| 2006/0030764 A1 | 2/2006 | Porges et al. |
| 2006/0210120 A1 | 9/2006 | Rowe et al. |
| 2006/0211922 A1 | 9/2006 | Al-Ali et al. |
| 2006/0211923 A1 | 9/2006 | Al-Ali et al. |
| 2006/0211924 A1 | 9/2006 | Smith et al. |
| 2006/0211925 A1 | 9/2006 | Lamego et al. |
| 2006/0211932 A1 | 9/2006 | Al-Ali et al. |
| 2006/0226992 A1 | 10/2006 | Al-Ali et al. |
| 2006/0229509 A1 | 10/2006 | Al-Ali et al. |
| 2006/0238358 A1 | 10/2006 | Al-Ali et al. |
| 2006/0241358 A1 | 10/2006 | Al-Ali et al. |
| 2006/0241363 A1 | 10/2006 | Al-Ali et al. |
| 2007/0149864 A1 | 6/2007 | Laakkonen |
| 2007/0185397 A1 | 8/2007 | Govari et al. |
| 2011/0009719 A1 | 1/2011 | Al-Ali et al. |
| 2011/0237914 A1 | 9/2011 | Lamego |
| 2012/0046530 A1 | 2/2012 | Al-Ali |
| 2012/0161970 A1 | 6/2012 | Al-Ali |
| 2012/0232359 A1 | 9/2012 | Al-Ali et al. |
| 2012/0232363 A1 | 9/2012 | Al-Ali et al. |

FOREIGN PATENT DOCUMENTS

| | | |
|---|---|---|
| EP | 0 675 541 | 10/1995 |
| EP | 1 080 683 | 3/2001 |
| EP | 1 207 536 A2 | 5/2002 |
| EP | 1 895 892 | 5/2010 |
| EP | 2 305 104 | 4/2011 |
| EP | 2 476 369 | 7/2012 |
| EP | 2 139 383 | 2/2013 |
| JP | 61-28172 | 2/1986 |
| JP | 62-000324 | 1/1987 |
| JP | 63-275327 | 11/1988 |
| JP | 64-500495 | 2/1989 |
| JP | 2-126829 | 5/1990 |
| JP | 2-145457 | 12/1990 |
| JP | 05-207993 | 8/1993 |
| JP | H05-200017 | 8/1993 |
| JP | 6-505903 | 7/1994 |
| JP | 6-237013 | 8/1994 |
| JP | 7-281618 | 10/1995 |
| JP | 07-325546 | 12/1995 |
| JP | 9-192120 | 7/1997 |
| JP | 10-216112 | 8/1998 |
| JP | 10-509352 | 9/1998 |
| JP | 10-269344 A | 10/1998 |
| JP | 10-295676 | 11/1998 |
| JP | 10-305026 | 11/1998 |
| JP | 11-163412 | 6/1999 |
| JP | 11-164826 | 6/1999 |
| JP | 11-506834 | 6/1999 |
| JP | 11-183377 | 7/1999 |
| JP | H11-508691 | 7/1999 |
| JP | 2000-116625 | 4/2000 |
| JP | 2002-516689 | 6/2002 |
| JP | 2002-228579 | 8/2002 |
| JP | 2002-525151 | 8/2002 |
| JP | 2002-315739 | 10/2002 |
| JP | 2003-507718 | 2/2003 |
| JP | 2003-084108 | 3/2003 |
| JP | 2003-521985 | 7/2003 |
| JP | 2004-070179 | 3/2004 |
| JP | 2004-510467 | 4/2004 |
| JP | 2004-226277 | 8/2004 |
| JP | 2004-296736 | 10/2004 |
| JP | 2004-532526 | 10/2004 |
| JP | 2004-327760 | 11/2004 |
| JP | 2005-501589 | 1/2005 |
| JP | 2005-253478 | 9/2005 |
| JP | 2008-505706 | 2/2008 |
| JP | 4879913 | 12/2011 |
| JP | 2012-110746 | 6/2012 |
| JP | 2012-130756 | 7/2012 |
| JP | 5096174 | 9/2012 |
| JP | 5166619 | 3/2013 |
| WO | WO 88/01150 | 2/1988 |
| WO | WO 88/02020 | 2/1988 |
| WO | WO 92/16142 | 10/1992 |
| WO | WO 95/16387 | 6/1995 |
| WO | WO 96/13208 | 5/1996 |
| WO | WO 96/41138 | 12/1996 |
| WO | WO 97/01985 | 1/1997 |
| WO | WO 98/43071 | 10/1998 |
| WO | WO 00/18290 | 4/2000 |
| WO | WO 00/42911 A1 | 7/2000 |
| WO | WO 00-59374 | 10/2000 |
| WO | WO 01/13790 | 3/2001 |
| WO | WO 01/30414 | 5/2001 |
| WO | WO 01/58347 | 8/2001 |
| WO | WO 02/17780 | 3/2002 |
| WO | WO 02/26123 | 4/2002 |
| WO | WO 02/089664 | 11/2002 |
| WO | WO 03/020129 | 3/2003 |
| WO | WO 03/068060 | 8/2003 |
| WO | WO 03/077761 | 9/2003 |
| WO | WO 2004/034898 | 4/2004 |
| WO | WO 2004/038801 | 5/2004 |
| WO | WO 2005/011488 | 2/2005 |
| WO | WO 2006/017117 | 2/2006 |
| WO | WO 2006/094168 | 9/2006 |
| WO | WO 2009/137524 A2 | 11/2009 |

OTHER PUBLICATIONS

European Examination Report dated Apr. 1, 2010, re EP App. No. 08 744 412.1-2319.

(56) References Cited

OTHER PUBLICATIONS

European Examination Report dated Mar. 18, 2011, re EP App. No. 08 744 412.1-2319.
European Examination Report dated Sep. 2, 2010, re EP App. No. 08 744 412.1-2319.
European Extended Search Report re EPO App. No. 10162402.1, SR dated Aug. 9, 2010.
Hall, et al., Jeffrey W.; Near-Infrared Spectrophotometry: A New Dimension in Clinical Chemistry; vol. 38; No. 9; 1992.
International Search Report for PCT/US2006/007516, mailed on Jan. 11, 2007, in 4 pages.
Japanese First Office Action (Notice of Reasons for Rejection), re JP App. No. 2007-558207, dated Jun. 28, 2011.
Japanese First Office Action (Notice of Reasons for Rejection), re JP App. No. 2007-558247, dated Jun. 28, 2011.
Japanese Office Action (Notice of Allowance), re JP App. No. 2007-558247, dated Oct. 24, 2011.
Japanese Office Action (Notice of Reasons for Rejection) re JP App. No. 2007-558246, dated Jun. 28, 2011.
Japanese Office Action (Notice of Reasons for Rejection), re JP App. No. 2007-558238, dated Jun. 28, 2011.
Japanese Office Action re JP Application No. 2007-558249, dated Jul. 13, 2011.
Japanese Office Action re JP Application No. 2007-558249, dated Nov. 8, 2011.
Japanese Office Action re JP Application No. JP 2007-558208, dated Aug. 23, 2011.
Japanese Office Action re JP Application No. JP 2007-558248, dated Nov. 8, 2011.
Japanese Office Action re JP Application No. 2007-558209, dated Oct. 25, 2011.
Japanese Office Action re JP Application No. 2007-558245, dated Oct. 25, 2011.
Kuenstner, et al., J. Todd; Measurement of Hemoglobin in Unlysed Blood by Near-Infrared Spectroscopy; vol. 48; No. 4, 1994.
Manzke, et al., B., Multi Wavelength Pulse OXimetry in the Measurement of Hemoglobin Fractions; vol. 2676, date unknown.
Naumenko, E. K.; Choice of Wavelengths for Stable Determination of Concentrations of Hemoglobin Derivatives from Absorption Spectra of Erythrocytes; vol. 63; No. 1; pp. 60-66 Jan.-Feb. 1996; Original article submitted Nov. 3, 1994.
Patent Cooperation Treaty (PCT) International Search Report; PCT/US 2006/007389; Date of Mailing Jul. 17, 2006; pp. 1-9.
PCT International Search Report; PCT/US2006/007506; Date of Mailing Jul. 17, 2006; pp. 1-10.
PCT International Search Report; PCT/US2006/007539; Date of Mailing Jul. 17, 2006; pp. 1-9.
PCT International Search Report; PCT-US2006-007387; Date of Mailing Jul. 17, 2006; pp. 1-9.
PCT International Search Report; PCT-US2006-007388; Date of Mailing Jul. 17, 2006; pp. 1-9.
PCT International Search Report; PCT-US2006-007536; Date of Mailing Jul. 17, 2006; pp. 1-9.
PCT International Search Report; PCT-US2006-007537; Date of Mailing Jul. 17, 2006; pp. 1-10.
PCT International Search Report; PCT-US2006-007538; Date of Mailing Jul. 17, 2006; pp. 1-9.
PCT International Search Report; PCT-US2006-007540; Date of Mailing Jul. 17, 2006; pp. 1-9.
PCT International Search Report; PCT-US2006-007958; Date of Mailing Jul. 17, 2006; pp. 1-8.
PCT Search Report of International Application No. PCT/US2008/058327, Mailing Date of Jun. 30, 2009, in 12 pages.
Schmitt, Joseph M.; Simple Photon Diffusion Anaylsis of the Effects of Multiple Scattering on Pulse Oximetry; Mar. 14, 1991; revised Aug. 30, 1991.
Schmitt, Joseph M.; Zhou, Guan-Xiong; Miller, Justin, Measurement of Blood Hematocrit by Dual-wavelength Near-IR Photoplethysmography, published May 1992, Proc. SPIE vol. 1641, p. 150-161, Physiological Monitoring and Early Detection Diagnostic Methods, Thomas S. Mang; Ed. (SPIE homepage), in 12 pages.
Schnapp, et al., L.M.; Pulse Oximetry. Uses and Abuses.; Chest 1990; 98; 1244-1250001 10.1378/Chest.98.5.1244.
European Examination Report, re EP Application No. 12163719.3, dated Feb. 6, 2013.
European Extended Search Report of European Application No. 12163719.3, dated of Jun. 18, 2012, in 6 pages.
European Office Action re EP Application No. 06 736 799.5, dated Nov. 30, 2012.
European Search Report, re EP Application No. 10 19 1029, dated Jun. 5, 2012.
Japanese Office Action, re JP Application No. 2012-045419, dated Jun. 26, 2012.
Japanese Office Action (Official Inquiry) re JP App. No. 2007-558246, dated Dec. 11, 2012.
Japanese Office Action (Reasons for Rejection) re JP App. No. 2007-558246, dated Nov. 1, 2011.
Japanese Office Action (Decision of Rejection), re JP Application No. JP 2007-558328, dated Jun. 25, 2013.
Japanese Office Action (Official Inquiry), re JP App. No. 2007-558238/Appeal No. 2012-004053, dated Dec. 11, 2012.
Japanese Office Action re JP Application No. JP 2007-558248, dated Nov. 27, 2012.
Japanese Office Action, re JP Application No. 2007-558237, dated Aug. 1, 2011.
Japanese Office Action, re JP Application No. JP 2007-558237, dated Oct. 16, 2012.
Japanese Office Action re JP Application No. 2007-558209, dated Oct. 30, 2012.
Japanese Office Action re JP Application No. 2007-558245, dated Jan. 15, 2013.
Japanese Final Office Action re Amendments re JP Application No. 2007-558249, dated Apr. 17, 2012.
Japanese Office Action re JP Application No. 2007-558249, dated Aug. 28, 2012.
International Preliminary Report on Patentability in US/2010/058981 dated Jun. 14, 2012.
PCT International Written Opinion and Search Report, re PCT App. No. PCT/US2006/007506, dated Jul. 17, 2006.

* cited by examiner

CONFIGURABLE PHYSIOLOGICAL MEASUREMENT SYSTEM

PRIORITY CLAIM TO RELATED PROVISIONAL APPLICATIONS

The present application is a continuation of U.S. patent application Ser. No. 11/367,036, filed Mar. 1, 2006, entitled "Configurable Physiological Measurement System," which claims priority benefit under 35 U.S.C. §119(e) to U.S. Provisional Patent Application Ser. No. 60/657,596, filed Mar. 1, 2005, entitled "Multiple Wavelength Sensor," No. 60/657,281, filed Mar. 1, 2005, entitled "Physiological Parameter Confidence Measure," No. 60/657,268, filed Mar. 1, 2005, entitled "Configurable Physiological Measurement System," and No. 60/657,759, filed Mar. 1, 2005, entitled "Noninvasive Multi-Parameter Patient Monitor." The present application incorporates the foregoing disclosures herein by reference in their entirety.

INCORPORATION BY REFERENCE OF CO-PENDING RELATED APPLICATIONS

The present application is related to the following co-pending U.S. utility applications:

| | App. Ser. No. | Filing Date | Title | Atty Dock. |
|---|---|---|---|---|
| 1 | 11/367,013 | Mar. 1, 2006 | Multiple Wavelength Sensor Emitters | MLR.002A |
| 2 | 12/422,915 | Apr. 13, 2009 | Multiple Wavelength Sensor Emitters | MLR.002C1 |
| 3 | 11/366,209 | Mar. 1, 2006 | Multiple Wavelength Sensor Substrate | MLR.004A |
| 4 | 12/568,469 | Sep. 28, 2009 | Multiple Wavelength Sensor Emitters | MLR.006C1 |
| 5 | 11/366,997 | Mar. 1, 2006 | Multiple Wavelength Sensor Drivers | MLR.009A |
| 6 | 11/367,034 | Mar. 1, 2006 | Physiological Parameter Confidence Measure | MLR.010A |
| 7 | 11/367,036 | Mar. 1, 2006 | Configurable Physiological Measurement System | MLR.011A |
| 8 | 11/367,033 | Mar. 1, 2006 | Noninvasive Multi-Parameter Patient Monitor | MLR.012A |
| 9 | 11/367,014 | Mar. 1, 2006 | Noninvasive Multi-Parameter Patient Monitor | MLR.013A |
| 10 | 11/366,208 | Mar. 1, 2006 | Noninvasive Multi-Parameter Patient Monitor | MLR.014A |
| 11 | 12/056,179 | Mar. 26, 2008 | Multiple Wavelength Optical Sensor | MLR.015A |
| 12 | 12/082,810 | Apr. 14, 2008 | Optical Sensor Assembly | MLR.015A2 |

The present application incorporates the foregoing disclosures herein by reference in their entirety.

BACKGROUND OF THE INVENTION

Spectroscopy is a common technique for measuring the concentration of organic and some inorganic constituents of a solution. The theoretical basis of this technique is the Beer-Lambert law, which states that the concentration $c_i$ of an absorbent in solution can be determined by the intensity of light transmitted through the solution, knowing the pathlength $d_\lambda$, the intensity of the incident light $I_{0,\lambda}$, and the extinction coefficient $\epsilon_{i,\lambda}$ at a particular wavelength $\lambda$. In generalized form, the Beer-Lambert law is expressed as:

$$I_\lambda = I_{0,\lambda} e^{-d_\lambda \cdot \mu_{a,\lambda}} \quad (1)$$

$$\mu_{a,\lambda} = \sum_{i=1}^{n} \varepsilon_{i,\lambda} \cdot c_i \quad (2)$$

where $\mu_{a,\lambda}$ is the bulk absorption coefficient and represents the probability of absorption per unit length. The minimum number of discrete wavelengths that are required to solve EQS. 1-2 are the number of significant absorbers that are present in the solution.

A practical application of this technique is pulse oximetry, which utilizes a noninvasive sensor to measure oxygen saturation ($SpO_2$) and pulse rate. In general, the sensor has light emitting diodes (LEDs) that transmit optical radiation of red and infrared wavelengths into a tissue site and a detector that responds to the intensity of the optical radiation after absorption (e.g., by transmission or transreflectance) by pulsatile arterial blood flowing within the tissue site. Based on this response, a processor determines measurements for $SpO_2$, pulse rate, and can output representative plethysmographic waveforms. Thus, "pulse oximetry" as used herein encompasses its broad ordinary meaning known to one of skill in the art, which includes at least those noninvasive procedures for measuring parameters of circulating blood through spectroscopy. Moreover, "plethysmograph" as used herein (commonly referred to as "photoplethysmograph"), encompasses its broad ordinary meaning known to one of skill in the art, which includes at least data representative of a change in the absorption of particular wavelengths of light as a function of the changes in body tissue resulting from pulsing blood. Pulse oximeters capable of reading through motion induced noise are available from Masimo Corporation ("Masimo") of Irvine, Calif. Moreover, portable and other oximeters capable of reading through motion induced noise are disclosed in at least U.S. Pat. Nos. 6,770,028, 6,658,276, 6,157,850, 6,002,952 5,769,785, and 5,758,644, which are owned by Masimo and are incorporated by reference herein. Such reading through motion oximeters have gained rapid acceptance in a wide variety of medical applications, including surgical wards, intensive care and neonatal units, general wards, home care, physical training, and virtually all types of monitoring scenarios.

SUMMARY OF THE INVENTION

A physiological measurement system has a sensor that transmits optical radiation at a multiplicity of wavelengths other than or including the red and infrared wavelengths utilized in pulse oximeters. The system also has a processor that determines the relative concentrations of blood constituents other than or in addition to $HbO_2$ and Hb, such as carboxyhemoglobin (HbCO), methemoglobin (MetHb), fractional oxygen saturation, total hemaglobin (Hbt) and blood glucose to name a few. Further, such a system may be combined with other physiological parameters such as noninvasive blood pressure (NIBP). There is a need to easily configure such a physiological measurement system from compatible components capable of measuring various physiological parameters.

DETAILED DESCRIPTION OF THE PREFERRED EMBODIMENTS

In this application, reference is made to many blood parameters. Some references that have common shorthand designations are referenced through such shorthand designations. For example, as used herein, HbCO designates carboxyhemoglobin, HbMet designates methemoglobin, and Hbt designates total hemoglobin. Other shorthand designations such as COHb, MetHb, and tHb are also common in the art for these same constituents. These constituents are generally reported in terms of a percentage, often referred to as saturation, relative concentration or fractional saturation. Total hemoglobin is generally reported as a concentration in g/dL. The use of the particular shorthand designators presented in this application does not restrict the term to any particular manner in which the designated constituent is reported.

Figure 1:
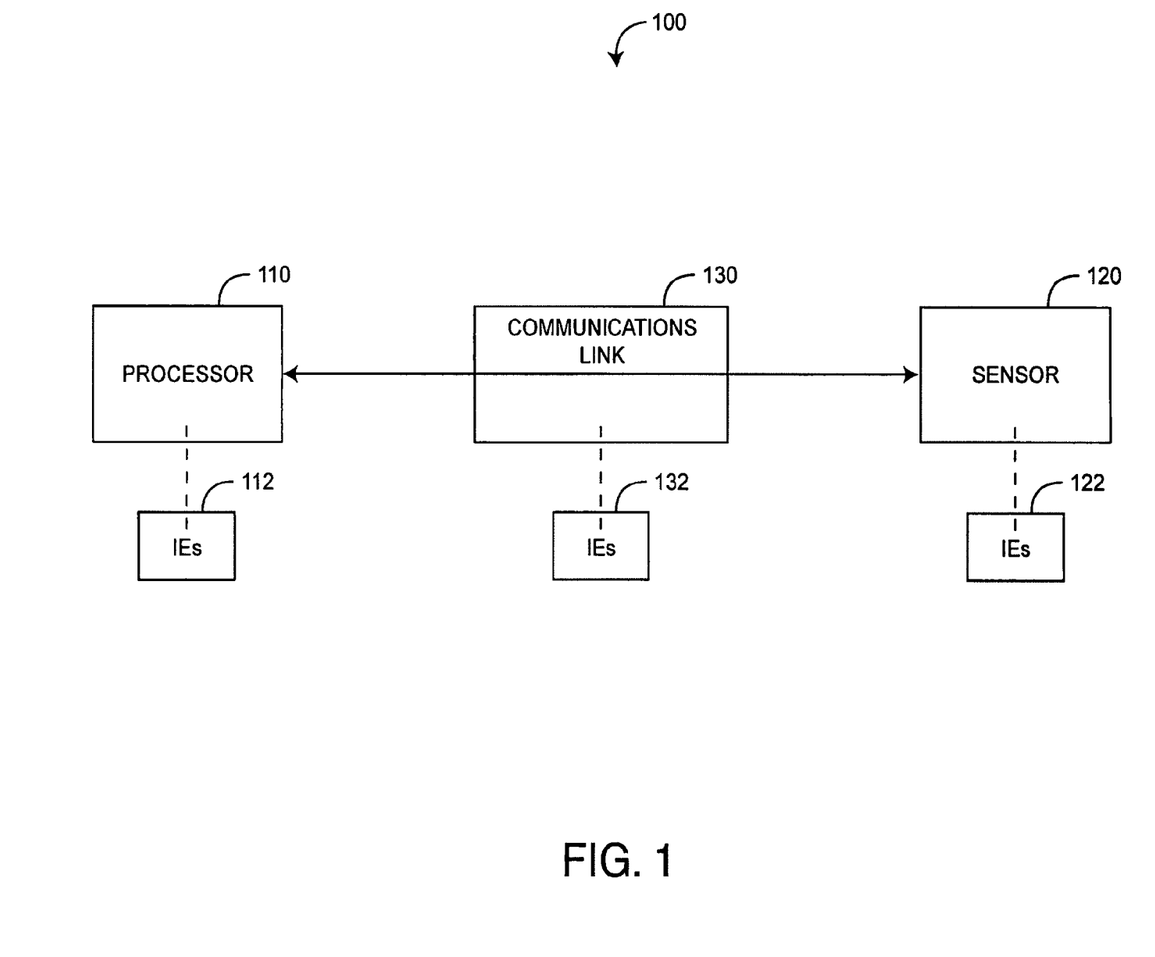
FIG. 1 is a general block diagram of a configurable physiological measurement system.

FIG. 1 illustrates a configurable physiological measurement system 100 having a processor 110, a sensor 120 and a communications link 130. In one embodiment, the sensor 120 has two or more light emitters that transmit optical radiation of two or more wavelengths into a tissue site and at least one detector that generates a signal responsive to the optical radiation after attenuation by the tissue site. Multiple wavelength sensors are described in U.S. patent application Ser. No. 10/719,928, entitled Blood Parameter Measurement System, assigned to Masimo Corporation, Irvine, Calif. and incorporated by reference herein.

The processor 110 generates drive signals so as to activate the sensor emitters and inputs and processes the corresponding detector signal so as determine the relative concentrations of two or more blood constituents. The communications link 130 provides communications between the processor 110 and sensor 120 including transmitting the drive signals from the processor 110 to the sensor 120 and the detector signals from the sensor 120 to the processor 110. In one embodiment, the communications link 130 is a cable and corresponding sensor and processor connectors that provide a wired connection between the processor 110 and connector 120. In another embodiment, the communications link 130 provides a wireless connection between the processor 110 and connector 120. The wireless connection may utilize Bluetooth®, IEEE 802.11 or similar wireless technologies.

As shown in FIG. 1, the configurable physiological measurement system 100 also has information elements 112, 122, 132 distributed across the processor 110, the sensor 120 and the communications link 130, which provide system configuration information, as described below. The information elements 112, 122, 132 may be memory devices, such as described below, or other active or passive electrical components. The information provided by the information elements 112, 122, 132 may be digital data stored in memory or component values determined by DC, AC or combinations of DC and AC voltages or currents. The information element 112, 122, 132 information may be determined by the processor 110 or by a reader or other device in communication with the information elements 112, 122, 132 and the processor 110.

Figure 2:
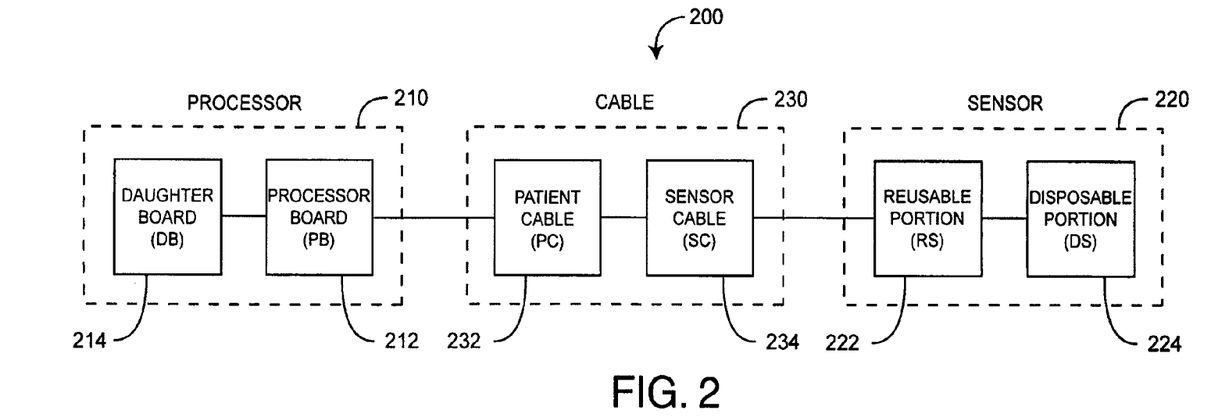
FIG. 2 is a detailed block diagram of a configurable physiological measurement system embodiment.

FIG. 2 illustrates configurable physiological measurement system embodiments having processor 210, sensor 220 and cable 230 components. In one embodiment, the processor 210 has a processor printed circuit board "board" 212 and an optional daughter board 214, which plugs into and expands the functionality of the processor board 212. For example, the daughter board 214 may be a noninvasive blood pressure (NIBP) controller that communicates with a blood pressure sensor and the processor board 212 so as to measure blood pressure parameters.

Also shown in FIG. 2, in one embodiment the sensor 220 is a "resposable" sensor comprising a reusable portion 222 and a disposable portion 224. In a particular embodiment, the reusable portion has at least one of a reusable emitter portion and a reusable detector portion, and the disposable portion 224 has at least one of a disposable emitter portion, a disposable detector portion and a disposable tape for attaching the reusable sensor 222 to a tissue site. A resposable sensor is described in U.S. Pat. No. 6,725,075 entitled Resposable Pulse Oximetry Sensor, assigned to Masimo Corporation and incorporated by reference herein.

Further shown in FIG. 2, in one embodiment the cable 230 is a patient cable 232 or a sensor cable 234 or a combination of a patient cable 232 and a sensor cable 234. A sensor cable 234 is fixedly attached at one end to a sensor and has a connector at the other end for attaching to a monitor or a patient cable. A patient cable 234 has connectors at both ends for interconnecting a sensor or sensor cable to a monitor.

Figure 3:
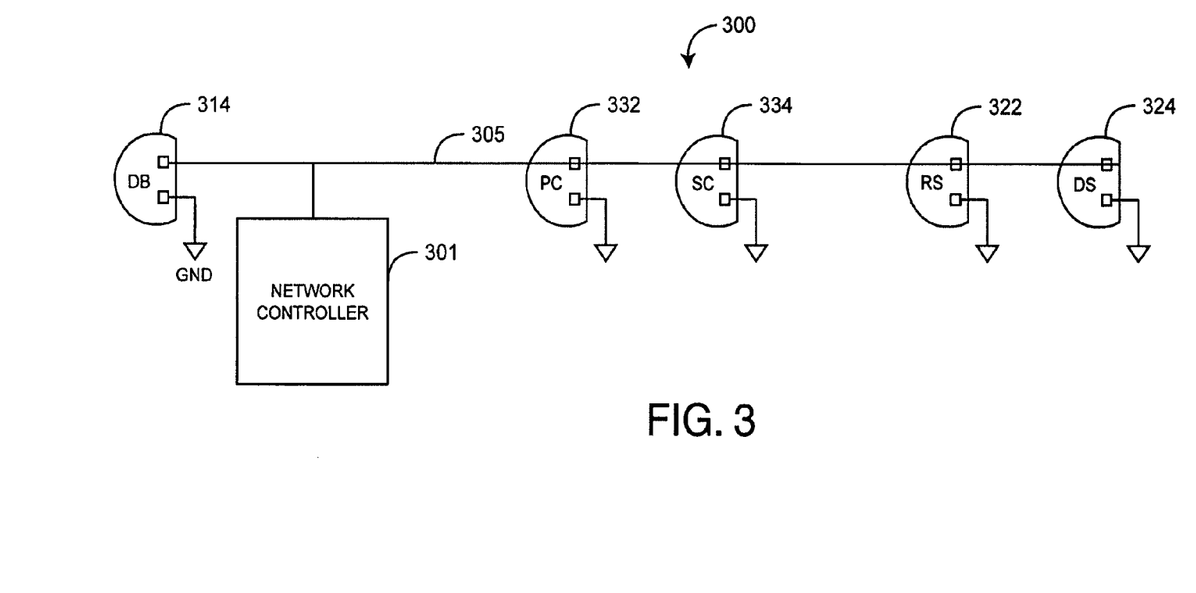
FIG. 3 is a detailed block diagram of networked information elements in a configurable physiological measurement system.

FIG. 3 illustrates an information element (IE) network 300 that advantageously enables a physiological measurement system 200 (FIG. 2) to be composed of various components 214-234 (FIG. 2) having, perhaps, differing parameter measurement capabilities, as described above. The IE network 300 also allows various components to "plug and play," i.e. interoperate without hardware or software modification, as described with respect to FIG. 4, below. Further, the IE network 300 provides for forward and backward compatibility between sensors and processors, as described with respect to FIGS. 5A-B, below.

As shown in FIG. 3, the IE network 300 has information elements 314-334, a network controller 301 and a communications path 305. In one embodiment, the network controller 301 resides on or is otherwise incorporated within a processor board 212 (FIG. 2). The information elements 314-334 correspond to the physiological measurement system components 210-230 (FIG. 2). In one embodiment, there may be zero, one, two or more information elements 314-334 on or within each physiological measurement system component 214-224 (FIG. 2). For example, the information elements 314-324 may include a DB element 314 mounted on a daughter board 214 (FIG. 2), a RS element 322 mounted within a reusable sensor portion 222 (FIG. 2), a DS element 324 mounted within a disposable sensor portion 224 (FIG. 2), a PC element 332 mounted within a patient cable 232 (FIG. 2) or connector thereof, and a SC element 334 mounted within a sensor cable 234 (FIG. 2) or connector thereof.

Also shown in FIG. 3, in one embodiment the information elements 314-334 are EPROMs or EEPROMs or a combination of EPROMs or EEPROMs within a particular component 210-230 (FIG. 2). In an advantageous embodiment, the communications path 305 is a single shared wire. This reduces the burden on the components 210-230 (FIG. 2) and associated connectors, which may have a relatively large number of conductors just for drive signals and detector signals when a multiplicity of sensor emitters are utilized for multiple parameter measurements. An information element 314-324 may be, for example, a Dallas Semiconductor DS2506 EPROM available from Maxim Integrated Products, Inc., Sunnyvale, Calif., or equivalent.

Figure 4:
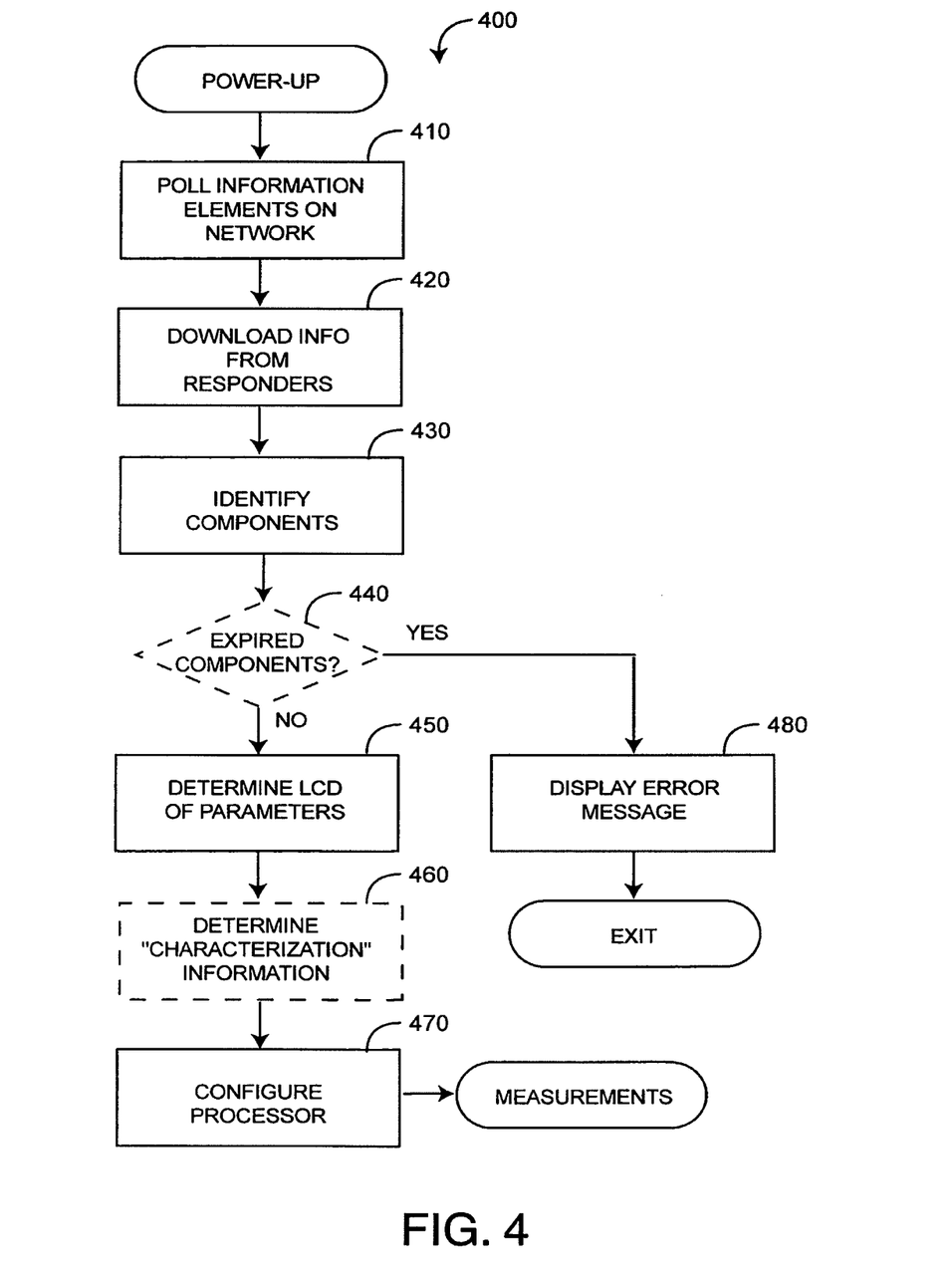
FIG. 4 is a flowchart of a physiological measurement system configuration process.

FIG. 4 illustrates a configuration process 400 for a physiological measurement system 200 (FIG. 2). This process is executed by the network controller 301 (FIG. 3) or the processor 210 (FIG. 2) or both with respect to information elements 314-334 (FIG. 3) that exist on the network 305 (FIG. 3). After system power-up, any information elements on the network are polled 410 so they identify themselves. Information is then downloaded from the responding information elements 420. In one embodiment, download information can be some or all of Identification (ID), Life, Parameters, Characterization and Features information. ID identifies a component on the network, either the type of component generally, such as a sensor or cable, or a particular part number, model and serial number, to name a few. As another example, ID for a disposable sensor portion 224 (FIG. 2) may be an attachment location on a patient and ID for a reusable sensor portion 222 (FIG. 2) may be a patient type.

Life, for example, may be a predetermined counter written into an EEPROM to indicate the number of uses or the length of use of a particular component. Then, Life is counted down, say each time power is applied, until a zero value is reached, indicating component expiration.

Parameters specifies the measurements the component is capable of supporting, which may include, for example, one or more of $SpO_2$, HbCO, MetHb, fractional $SpO_2$, Hbt, NIBP and blood glucose to name just a few. With respect to a sensor, Parameters depend on the number of emitters, emitter wavelength and emitter configuration, for example. For a cable, Parameters depend on the number of conductors and connector pinouts, for example. Parameters may also simply reflect a license to use a component, such as disposable tape, with respect to a particular system configuration.

Features set the mode for the processor or other system elements. As one example, Features specify the mode or modes of one or more algorithms, such as averaging.

Characterization allows the processor to "plug and play" with a particular component. For example, if the component is a sensor, Characterization may include information necessary to drive the emitters, such as the LED wavelengths and drive pattern. Characterization may also include calibration data for the parameters measured. As another example, Characterization for a sensor component 220 (FIG. 2) may indicate sensitivity to a probe-off condition depending on the sensor type. Probe-off detection is described in U.S. Pat. No. 6,654,624 entitled Pulse Oximeter Probe-Off Detector and U.S. Pat. No. 6,771,994 entitled Pulse Oximeter Probe-Off Detection System, both assigned to Masimo Corporation and incorporated by reference herein.

As shown in FIG. 4, components are identified 430 from downloaded ID information. If any of the information elements provide Life information, a check is made to determine if the corresponding component is expired 440. If so, an error message is displayed 480. The message may be a warning to replace the component or it may indicate that the system is nonfunctional. Next, the least common denominator (LCD) of the parameters is determined 450 from the Parameters information. This is described in further detail with respect to FIGS. 5A-B. Characterization is determined 460, if necessary for a particular component, such as a daughterboard or sensor. Finally, the processor is configured 470 and the system is ready to begin parameter measurements.

Figure 5A:
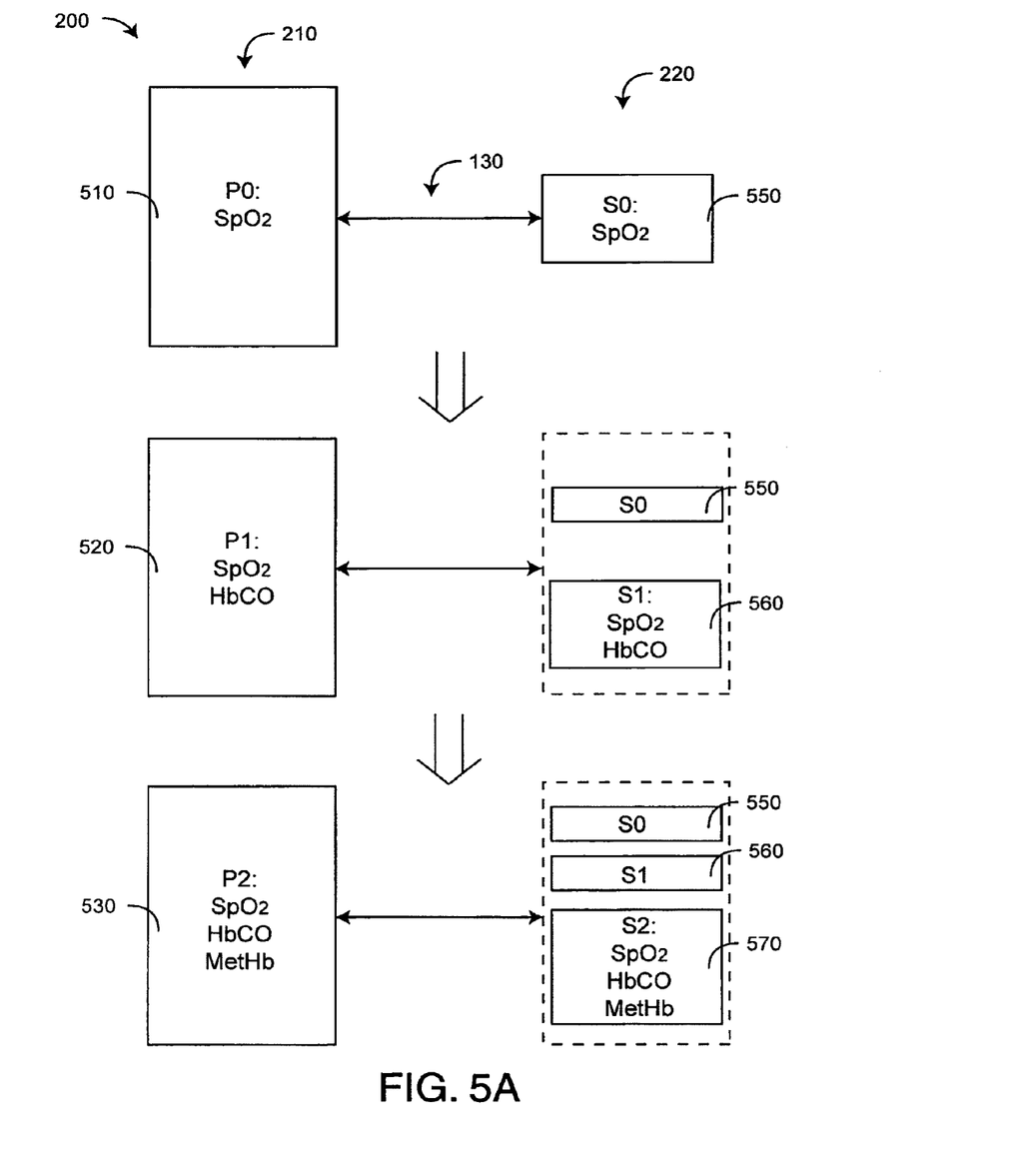
FIGS. 5A-B are block diagrams illustrating forward and backward sensor compatibility with various processors.
Figure 5B:
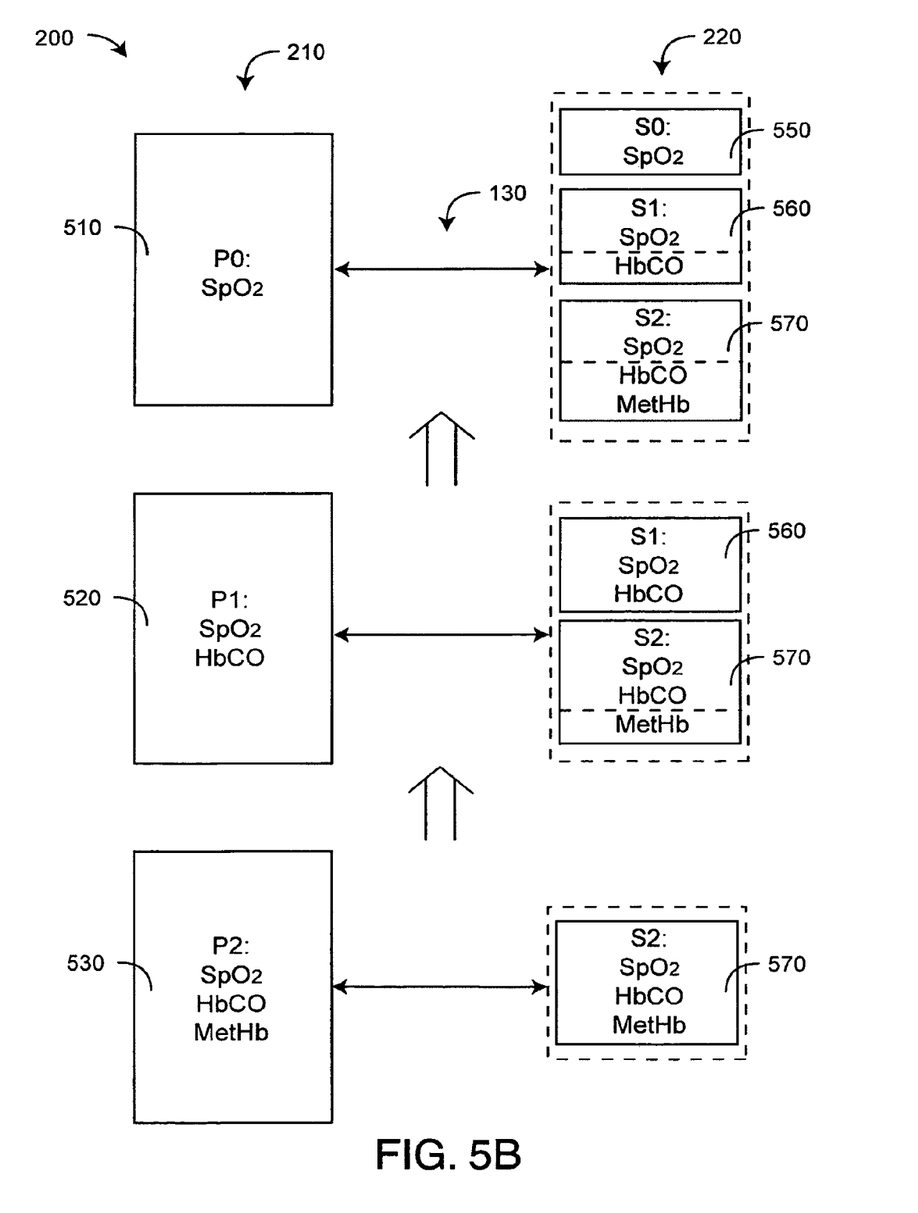

FIGS. 5A-B illustrate embodiments of a configurable physiological measurement system 100 demonstrating both forward sensor compatibility (FIG. 5A), and backward sensor compatibility (FIG. 5B). Further, the parameter measurement capability of each system 100 is determined by the least common denominator (LCD) of the parameter capabilities of a processor 210 and a sensor 220.

As shown in FIG. 5A, configurable physiological measurement systems 200 comprise a family of processors (P0, P1, P2) 210 including those capable of computing $SpO_2$ 510-530, HbCO 520-530 and MetHb 530. The systems 200 also comprise a family of sensors 220 (S0, S1, S2) including those capable of detecting $SpO_2$ 550-570, HbCO 560-570 and MetHb 570. Here, the lower numbered processors and sensors represent less capability, e.g. older generation processors and sensors or current generation, but less costly processors and sensors. Illustrated is forward sensor compatibility, i.e. less capable sensors are capable of running on more capable processors. For example, an $SpO_2$ only sensor 550 is capable of working with a multiple parameter ($SpO_2$, HbCO, MetHb) processor 530. Also illustrated is LCD functionality. A system 200 having a P2 processor 530 and a S0 sensor 550 is functional but only capable of measuring $SpO_2$.

FIG. 5B illustrates backward sensor compatibility, i.e. more capable sensors are capable of running on less capable processors. For example, a multiple parameter ($SpO_2$, HbCO, MetHb) sensor 570 is capable of working with an $SpO_2$ only processor 510. Also, a system 200 having a P0 processor 510 and a S2 sensor 570 is functional, but only capable of measuring $SpO_2$.

Forward and backward sensor compatibility is described above with respect to configurable physiological measurement systems 200 having various processor 210 capabilities and sensor 220 capabilities. The configurable physiological measurement systems 200 can have any or all of the processor 210, sensor 220 and cable 230 components described with respect to FIG. 2, above. As such forward and backward compatibility is equally applicable to combinations of processor 210 and cable 230 or combinations of sensor 220 and cable 230, including the components of such described with respect to FIG. 2, where the capability of such combinations is determined by LCD functionality, as described above.

A configurable physiological measurement system has been disclosed in detail in connection with various embodiments. These embodiments are disclosed by way of examples only and are not to limit the scope of the claims that follow. One of ordinary skill in the art will appreciate many variations and modifications.

What is claimed is:

1. A physiological measurement system comprising:
   a sensor configured to transmit light having a plurality of wavelengths into a tissue site and to generate a sensor signal responsive to the transmitted light after tissue attenuation; and
   a configurable processor configured to:
   receive automatically reported information regarding measurement capabilities of two or more components of the physiological measurement system, each of the two or more components including information elements configured to store information regarding at least measurement capabilities of the component;
   determine, based on the information received, which of a plurality of potential measurements the physiological measurement system is capable of measuring; and
   configure itself to calculate measurements of at least one of the plurality of potential measurements based on the determination.

2. The physiological measurement system of claim 1, wherein the automatically reported information comprises characterization information.

3. The physiological measurement system of claim 2, wherein the characterization information comprises characterization information related to a particular component of the physiological measurement system.

4. The physiological measurement system of claim 3, wherein the particular component comprises a daughterboard.

5. The physiological measurement system of claim 3, wherein the particular component comprises a sensor.

6. The physiological measurement system of claim 1, wherein the automatically reported information comprises information including a measurement capability of each component of the physiological measurement system.

7. A method of configuring a physiological parameter system, the method comprising:
   transmitting light having a plurality of wavelengths into a tissue site using a physiological sensor;
   generating a sensor signal responsive to the transmitted light after tissue attenuation;
   receiving, at a configurable processor, automatically reported information regarding one or more measurement capabilities of each of a plurality of components of the physiological parameter system including the physiological sensor, each of the plurality of components including an information element configured to store at least measurement capability information;
   determining, based on the information received, which of a plurality of potential measurements the physiological parameter system is capable of measuring; and
   configuring the processor to measure the one or more of the plurality of potential measurements which the physiological parameter system is capable of measuring.

8. The method of claim 7, wherein the received automatically reported information comprises characterization information.

9. The method of claim 8, wherein the characterization information comprises characterization information related to a particular component of the physiological parameter system.

10. The method of claim 9, wherein the particular component comprises a daughterboard.

11. The method of claim 9, wherein the particular component comprises a sensor.

12. The method of claim 7, wherein the received automatically reported information comprises information including a measurement capability of each component of the physiological parameter system.

13. A physiological measurement system comprising:
   a sensor configured to transmit light having a plurality of wavelengths into a tissue site and to generate a sensor signal responsive to the transmitted light after tissue attenuation; and
   means for receiving reported information regarding one or more measurement capabilities of each of two or more components of the physiological measurement system, determining, based on the information received, which of a plurality of potential measurements the physiological measurement system is capable of measuring, and automatically configuring a processor to calculate measurements of one or more of the plurality of potential measurements based on the determination,
   wherein each of the two or more components of the physiological measurement system includes an information element configured to store at least measurement capability information.

14. The physiological measurement system of claim 13, wherein the received reported information comprises characterization information.

15. The physiological measurement system of claim 14, wherein the characterization information comprises characterization information about a particular component of the physiological measurement system.

16. The physiological measurement system of claim 15, wherein the particular component comprises a daughterboard.

17. The physiological measurement system of claim 15, wherein the particular component comprises a sensor.

18. The physiological measurement system of claim 13, wherein the received reported information comprises information including a measurement capability of each component of the physiological measurement system.

* * * * *